(12) United States Patent
Lavi

(10) Patent No.: US 9,271,775 B2
(45) Date of Patent: Mar. 1, 2016

(54) SMALL JOINT FUSION IMPLANT

(75) Inventor: Abraham Lavi, Lakewood Ranch, FL (US)

(73) Assignee: Vilex in Tennessee, Inc., McMinville, TN (US)

( * ) Notice: Subject to any disclaimer, the term of this patent is extended or adjusted under 35 U.S.C. 154(b) by 460 days.

(21) Appl. No.: 12/462,662

(22) Filed: Aug. 6, 2009

(65) Prior Publication Data
US 2010/0036439 A1 Feb. 11, 2010

Related U.S. Application Data

(60) Provisional application No. 61/188,208, filed on Aug. 7, 2008.

(51) Int. Cl.
*A61B 17/86* (2006.01)
*A61B 17/72* (2006.01)
*A61B 17/84* (2006.01)
*A61B 17/68* (2006.01)
*A61B 17/00* (2006.01)

(52) U.S. Cl.
CPC ......... *A61B 17/8685* (2013.01); *A61B 17/7216* (2013.01); *A61B 17/7225* (2013.01); *A61B 17/7291* (2013.01); *A61B 17/84* (2013.01); *A61B 17/86* (2013.01); *A61B 2017/00477* (2013.01); *A61B 2017/681* (2013.01)

(58) Field of Classification Search
CPC .. A61B 17/58; A61B 17/68; A61B 2017/681; A61B 17/7216; A61B 17/7225; A61B 17/7291; A61B 17/84; A61B 17/86; A61B 17/8685
USPC .......... 606/300–321, 328, 86 R, 105; 411/389
See application file for complete search history.

(56) References Cited

U.S. PATENT DOCUMENTS

| | | | | | |
|---|---|---|---|---|---|
| 4,059,102 | A | * | 11/1977 | Devas | 606/309 |
| 5,417,692 | A | * | 5/1995 | Goble et al. | 606/311 |
| 5,643,267 | A | * | 7/1997 | Hitomi et al. | 606/62 |
| 6,077,262 | A | * | 6/2000 | Schlapfer et al. | 606/305 |
| 6,413,260 | B1 | * | 7/2002 | Berrevoets et al. | 623/16.11 |
| 2007/0259315 | A1 | * | 11/2007 | Last-Pollak | 433/201.1 |
| 2008/0281424 | A1 | * | 11/2008 | Parry et al. | 623/17.16 |
| 2009/0093820 | A1 | * | 4/2009 | Trieu et al. | 606/103 |

* cited by examiner

*Primary Examiner* — Larry E Waggle, Jr.
(74) *Attorney, Agent, or Firm* — Barbara E. Johnson, Esq.

(57) ABSTRACT

A two-component system for joining two bones or bone fragments, in which a first component is threaded, self-tapping and bears an annular mating end to engage two mating pins on the end of a second component which is also threaded and self-tapping. The two components have opposite handed threads thereon, so that upon final installation into adjacent bone the final rotation brings the abutted bone surfaces into a compressive engagement as each components burrows deeper into its respective bone surface.

1 Claim, 9 Drawing Sheets

SMALL JOINT FUSION IMPLANT

CROSS-REFERENCE TO RELATED APPLICATIONS

This patent application claims priority to U.S. Provisional Patent Application No. 61/188,208 filed Aug. 7, 2008, which is hereby incorporated herein by reference.

BACKGROUND OF THE INVENTION

1. Field of the Invention

The invention pertains to surgical bone implants for use in fusing two small bone segments (or two ends of a joint) primarily in the hand or the foot, or in any anatomic location in which two bones or bone fragments need to be positioned and secured together.

2. Orientation to the Prior Art

Particularly in podiatric surgery but also throughout orthopedic surgery generally, bringing two bones into desired tight or fused alignment has been challenging and often elusive, particularly with small bones such as in the foot. Prior art connecting devices for small bones have included, without limitation, the "Self-Tapping Screw for Small-Bone Surgery" disclosed and claimed in U.S. Pat. No. 7,037,309. In the patent specification of U.S. Pat. No. 7,037,309, moreover, there is further mention of the prior art "Barouk screw." According to the authors of U.S. Pat. No. 7,037,309, a Barouk screw is generally made of titanium and has a threaded proximal head and a threaded distal shank, and the screw thread of the head has a smaller pitch than that of the distal part, to make the screw self-compressing as to two adjacent bones through which it passes.

Generally, prior known systems for bringing bones into alignment, osteosynthesis or fusion have been less than optimal in that they provide materials which are not implanted from between the two pieces of bone to be joined, or because they involve implants which cannot be removed from the bone without causing serious damage to the bone. A need thus remains for a joint fusion system, particularly a small joint fusion system, in which bone screws are designed to be implanted from the interface of two small bones to be joined and which screws can be removed from the bone as necessary while minimizing damage to the bone.

SUMMARY OF THE INVENTION

In order to meet this need, the present implant includes two main bone screw components, "D" and "G," wherein the "D" component has right-handed screw threads of appropriate geometry on one end and on the other end possesses a cavity that accepts the free end of the "G" component. The "G" component has screw threads which are left handed. (Alternatively, "D" and "G" as described herein can be left- and right-handed, respectively, although such variation is not shown in the accompanying Figures.) Each of "D" and "G" is used with the other, with each being implanted in one of the two adjacent surfaces of an osteotomy or joint to be joined. The "D" component has two L-shaped slots at its free end. The "G" component has two mating pins at its free end and a screwdriver slot. The two components of the implant are then coupled by driving the components so that their free ends are a little below the bone surface, so that upon initial mating implanted components do not fully abut. Moreover, the position of one component is initially, during implantation, "biased" with respect to the other a significant fraction of a turn. At final installation, therefore, the surgeon must turn one of the fragments to align the slots with the mating pins. After the pins enter the slots, the surgeon pushes the two bone segments towards each other and when no further advance is possible the two bones are rotated in opposite directions to force the mating pins into the bottom of the "L" shaped slots in the "D" component. This final rotation reverses the initial rotational bias by turning the two bones in opposite directions to restore the natural orientation of the bones. Because the threads of one component are left-handed and the threads of the other component are right-handed, the final turning of the bone fragments results in driving the implant components deeper into their respective bones, thus creating a compressive force at the interface of the two bone surfaces to be joined. An important feature of the device is that the implantations are reversible without destroying the bone to remove the implant-regardless of which embodiment of the present invention is used, the joint is simply reopened as needed and the implanted components are unscrewed from their respective bones or bone fragments.

DESCRIPTION OF THE PREFERRED EMBODIMENTS

The present implant includes two main bone implant (screw) components, "D" and "G," wherein the "D" component has right-handed screw threads of appropriate geometry on one end and on the other end possesses a cavity that accepts the free end of the "G" component. The "G" component has screw threads which are left handed. (Alternatively, "D" and "G" as described herein can be left- and right-handed, respectively, although such variation is not shown in the accompanying Figures.) Each of "D" and "G" is used with the other, with each being implanted in one of the two adjacent surfaces of an osteotomy or joint to be joined. The "D" component has two L-shaped slots at its free end. The "G" component has two mating pins at its free end and a screwdriver slot. The two components of the implant are then coupled by driving them so that their free ends are a little below the bone surface, whereupon during initial mating the implanted components do not yet fully abut. Moreover, the position of one component is initially, during implantation, "biased" with respect to the other a significant fraction of a turn. At final installation, therefore, the surgeon must turn one of the fragments to align the slots with the mating pins. After the pins enter the slots, the surgeon pushes the two bone segments towards each other and when no further advance is possible the two bones are rotated in opposite directions to force the mating pins into the bottom of the "L" shaped slots in the "D" component. This rotation reverses the initial rotational bias by turning the two bones in opposite directions to restore the natural orientation of the bones. Because the threads of one component are left-handed and the threads of the other component are right-handed, this final turning of the bone fragments results in driving the implant components deeper into their respective bones, thus creating a compressive force where the two bone surfaces meet. An important feature of the device is that the implantations are reversible without destroying the bone to remove the implant—regardless of which embodiment of the present invention is used, the joint is simply reopened as needed and the implanted components are unscrewed from their respective bones or bone fragments.

Figure 1:
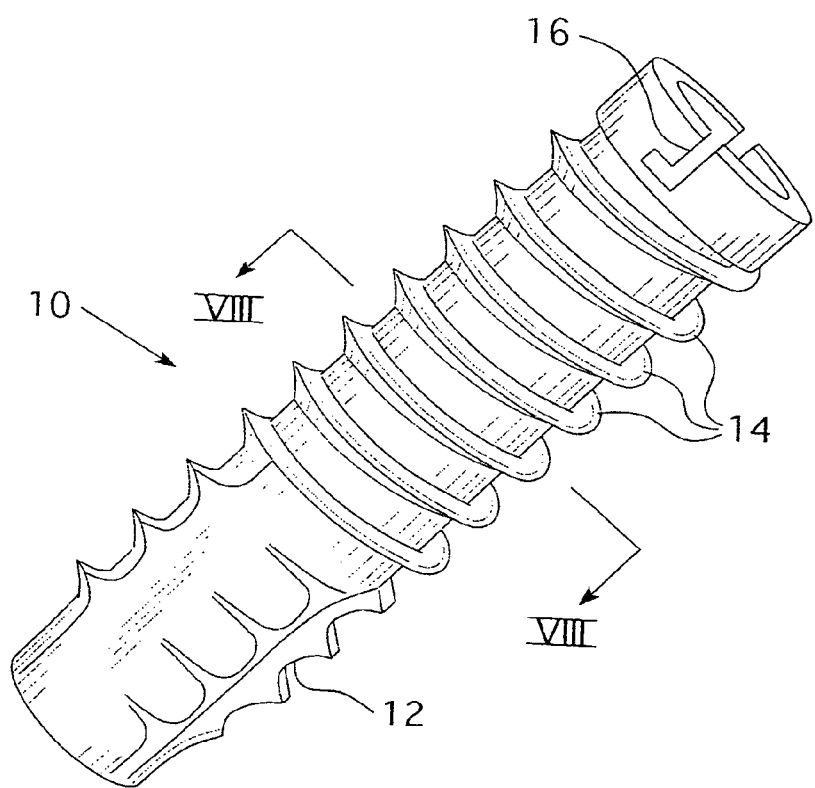
FIG. 1 is a perspective view of a "D" component of a two-component bone implant according to the invention.

Referring now to FIG. 1, a "D" component according to the present invention is shown in perspective. ("D" rather arbitrarily stands for "Droite," to indicate the typical (but not strictly necessary) right-handed screw threads born by the "D" component.) The D component 10 has a self-tapping distal end 12 of D component 10, with main threads 14 of the D component 10 having right-handed orientation as shown. The proximal end of D component 10 is annular with two opposing L shaped slots 16 designed to accept mating pins described below.

Figure 2:
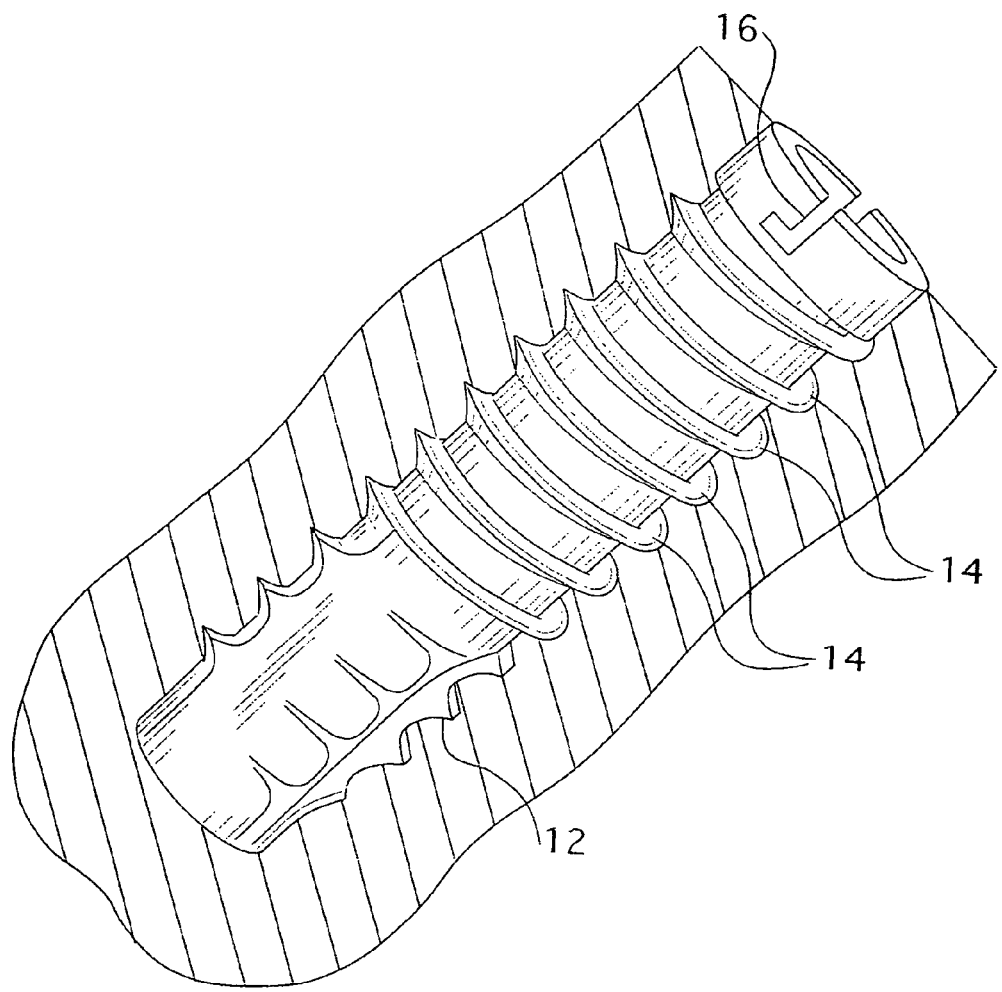
FIG. 2 is a perspective view of the "D" component of FIG. 1 encased by adjacent bone tissue shown in section.

FIG. 2 shows the same D component 10 of FIG. 1 approaching its final position in a bone or bone fragment. Ultimately, D component is inserted in its bone or bone fragment to a depth deeper than the surface of the bone or bone fragment to be joined.

Figure 3:
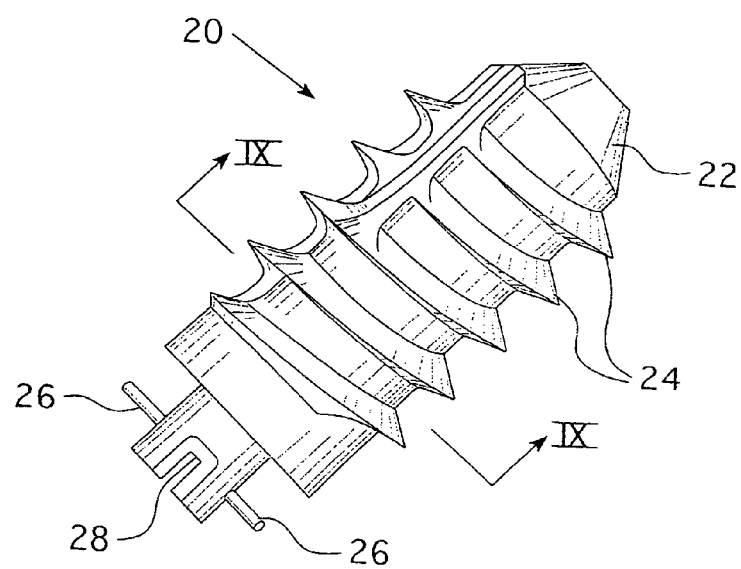
FIG. 3 is a perspective view of a "G" component of a two-component bone implant according to the invention.

FIG. 3 is a perspective view of a G component 20 according to the invention ("G" representing "Gauche" and the typical left-handed orientation of the screw threads thereon). G component 20 has a self-tapping distal end 22, main threads 24 and a proximal portion dimensioned to mate with the proximal end of D component and bearing mating pins 26 and screwdriver slot 28. Although the proximal end of D component 20 is shown as having a diameter smaller than the diameter of D component 20 along the middle of its shaft, this smaller dimension is not necessary as long as the dimension mates with the adjacent proximal portion of D component 10, because the dimensions of the proximal portion of D component 10 may also vary.

Figure 4:
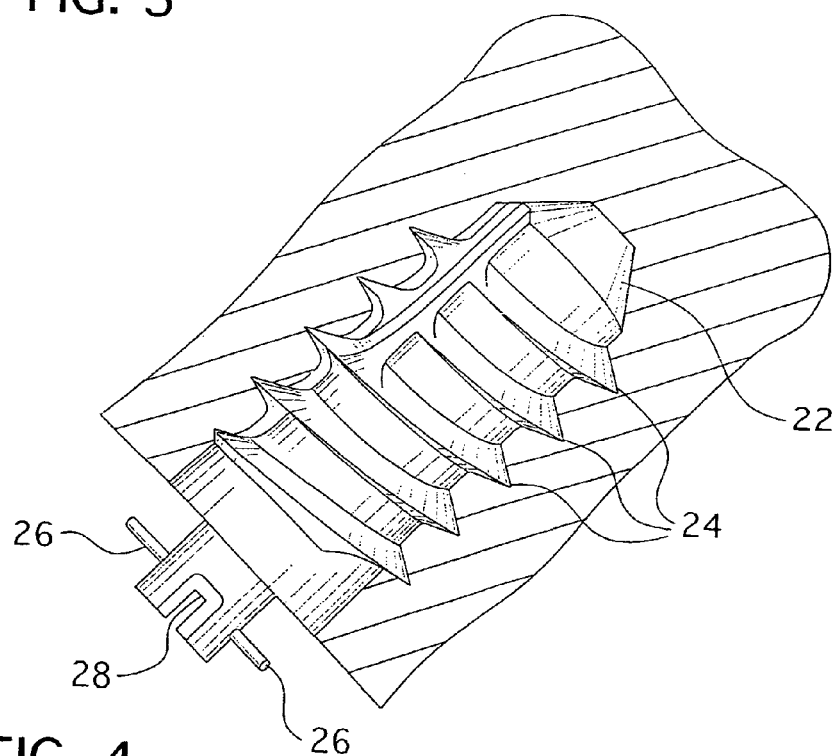
FIG. 4 is a perspective view of the "G" component of FIG. 3 encased by adjacent bone tissue shown in section.

FIG. 4 illustrates the G component 20 of FIG. 3 approaching its final position in a bone or bone fragment to be joined to another bone or bone fragment.

Figure 5:
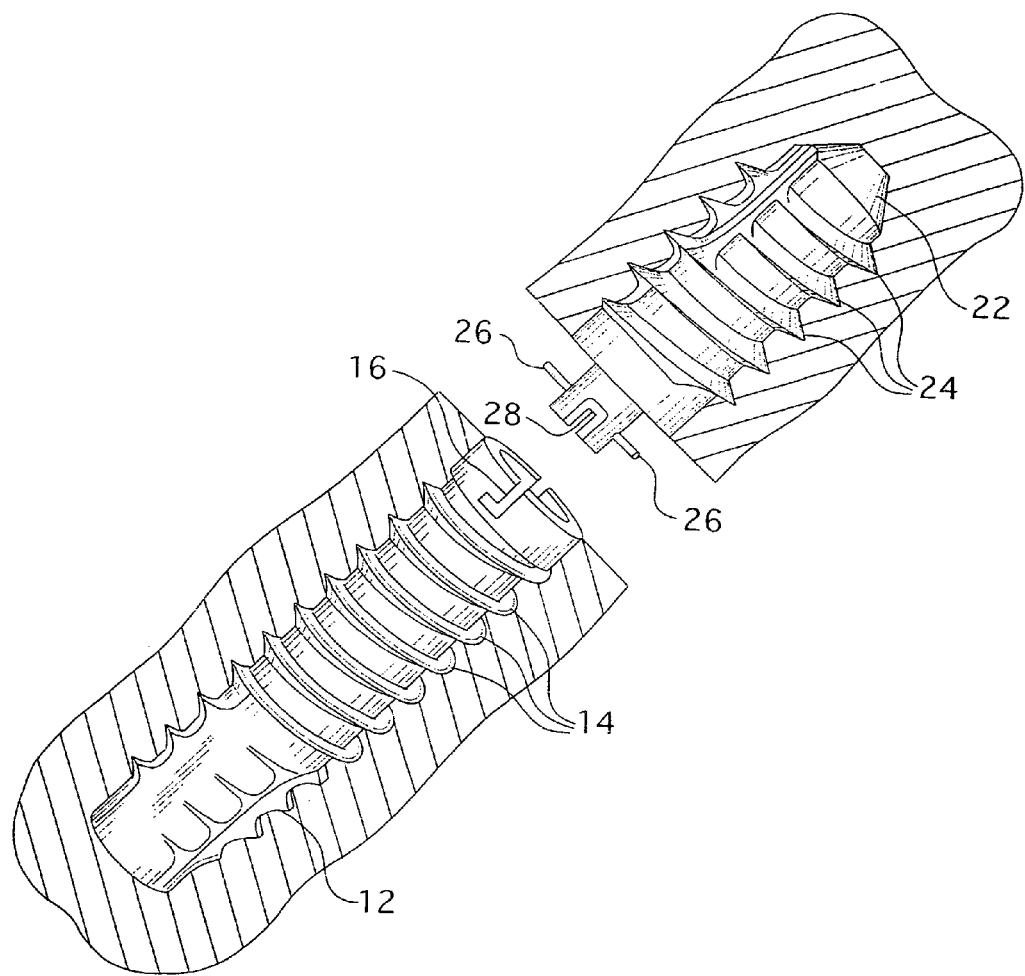
FIG. 5 is a perspective view of both the "D" and "G" components of the invention as positioned in adjacent bone (shown in section) during the implantation procedure.
Figure 6:
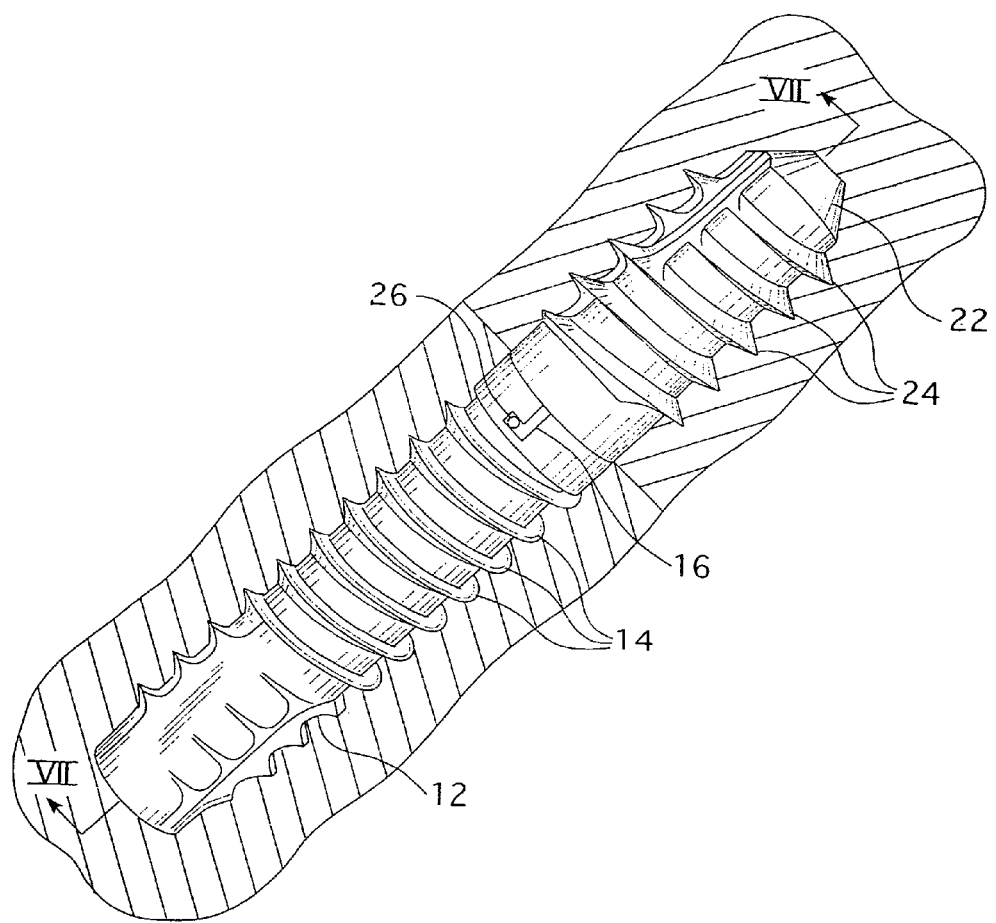
FIG. 6 is a perspective view of the "D" and "G" components after the implantation procedure is complete.

FIG. 5 illustrates the D component 10 of FIG. 3 and the G component 20 of FIG. 4 as they approach one another during a bone fusion procedure. FIG. 6 shows the D and G components 10 and 20 of FIG. 5 in final position after the components are mated and finally rotated into place. In FIG. 6, the D component 10 and the G component 20 are actually positioned deeply enough in the bones that after the final turn of the D and G components 10 and 20 to secure them the final turn actually drives the D and G components 10 and 20 even further into their respective bones or bone fragments. This action creates a compressive junction of the adjacent bones or bone fragments, which thus do not merely abut but actually compressively engage with a force commensurate to that applied upon final tightening and embedding of D and G components.

Figure 7:
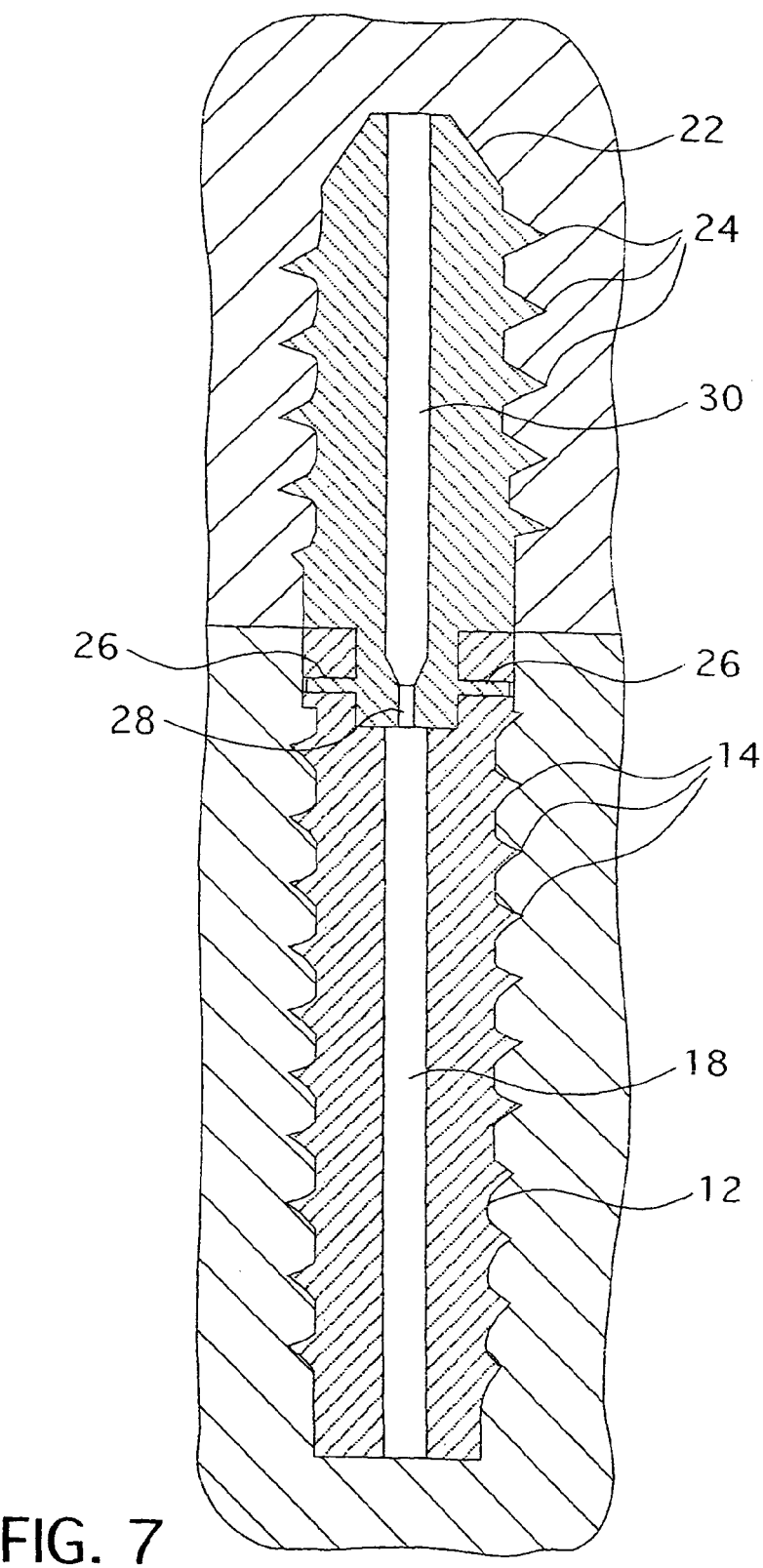
FIG. 7 is a sectional view taken along lines VII-VII of FIG. 6.

FIG. 7 is a sectional view along lives VII-VII of FIG. 6. FIG. 7 illustrates one of many optional cannulation configurations whereby an aperture may run the length of either or both of D or G components 10 or 20. The cannulation is completely optional. In the smallest sizes of bone implants according to the present invention, for strength reasons the cannulations are omitted. However, in larger bone screws according to this invention the cannulations both reduce weight and provide an aperture which can be used to follow a pre-positioned guide wire in the bone. For example, to perform a metatarsaphalangeal fusion a surgeon can insert a guide wire, with the guide wire acting as a bone drill, into and through the proximal phalange right through the adjacent middle and distal phalange so that the guide wire exits the toe tip just under the toenail. Assuming the protruding guide wire is centered, confirming a straight drill path through the phalanges, the surgeon may then remove the guide wire and re-run the guide wire "in retrograde," that is, straight back in from the aperture formed at the tip of the toe under the nail and back through all three phalanges to bore straight through the metatarsal to create a straight metatarsaphalangeal bore. This procedure assures straight alignment of the metatarsal and proximal phalange, in preparation for a metatarsaphalangeal fusion. When the D and G components 10 and 20 of the present invention are cannulated, each can be installed by implanting them over any guide wire present in the bone to assure straight positioning of the component. Guide wires, when used at all, may be removed or left in place; the use of guide wires in orthopedic surgery is well known in the art at this writing. When only one or the other of the D or G components is cannulated, then of course only the corresponding guide wire is used, or neither cannulations nor guide wires are necessary if the surgeon aligns the inventive implants using other techniques.

Figure 8:
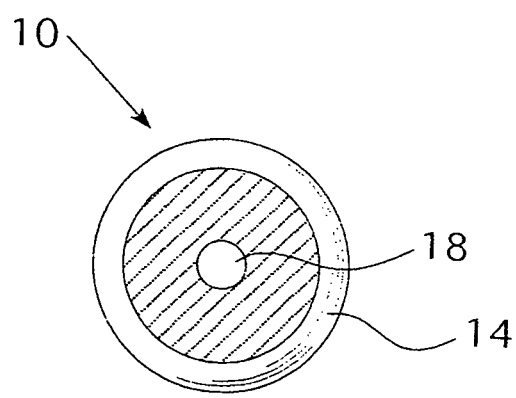
FIG. 8 is a sectional view taken along lines VIII-VIII of FIG. 1.
Figure 9:
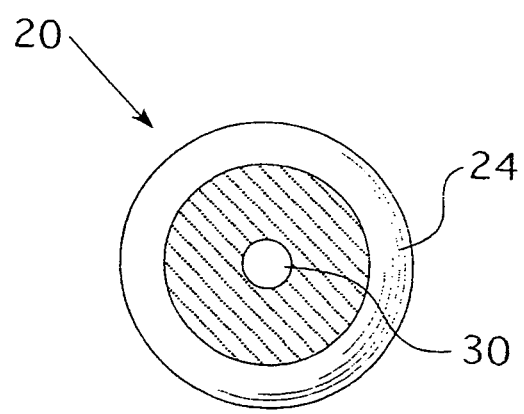
FIG. 9 is a sectional view taken along lines IX-IX of FIG. 3.

FIG. 8 is a sectional view along lines VIII-VIII of FIG. 1, showing the optional cannulation 18. FIG. 9 is a sectional view along lines IX-IX of FIG. 3, showing the optional cannulation 30. Optional cannulations 18 and 30 are also shown in the section illustrated in FIG. 7.

Figure 10:
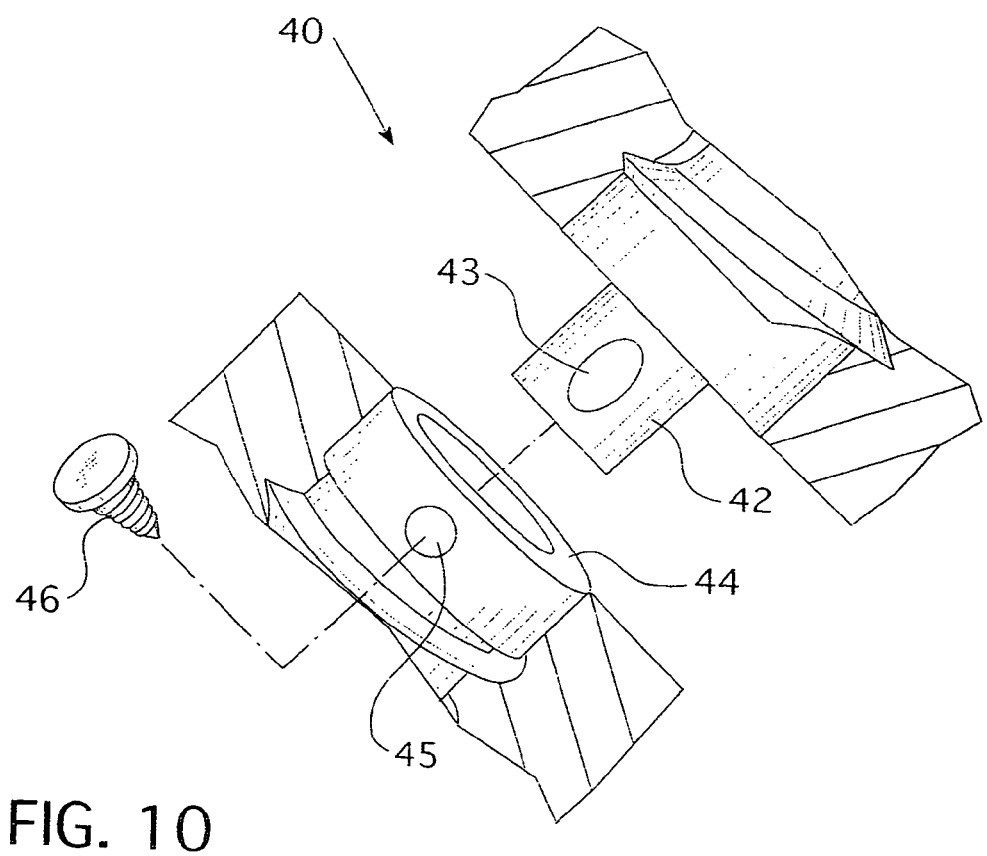
FIG. 10 is a perspective view of a second embodiment of the invention having an alternative interface coupling arrangement.

FIG. 10 illustrates a second embodiment 40 of the invention having an alternative interface coupling arrangement. This alternative is different from the pins-and-slots coupling arrangements described above. In FIG. 10, the upper interface 42 contains an upper interface elliptical aperture 43 part-way or completely through the upper interface 42. For example, if the upper interface 42 is annular, the upper interface elliptical aperture 43 extends through at least one of the annular walls; if the upper interface is solid, the upper interface elliptical aperture 43 extends part-way or completely through the upper interface 42. The lower interface 44 is annular and at least one wall of the lower interface 44 includes a lower interface circular aperture 45. The two apertures receive a tapered screw 46 to secure and to draw the upper interface 42 and the lower interface 44 together. As the tapered screw 46 advances through the lower interface circular aperture 45 and then through the upper interface elliptical aperture 43, the upper interface 42 is drawn (pulled) further into engagement with the lower interface 44 as the upper interface 42 moves to allow the upper interface elliptical aperture 43 to accommodate the increasing diameter of the tapered screw 46 as it is inserted. The net effect is to produce a compression force at the interface of the two bone segments on both sides of the joint or bone pieces to be joined.

Figure 11:
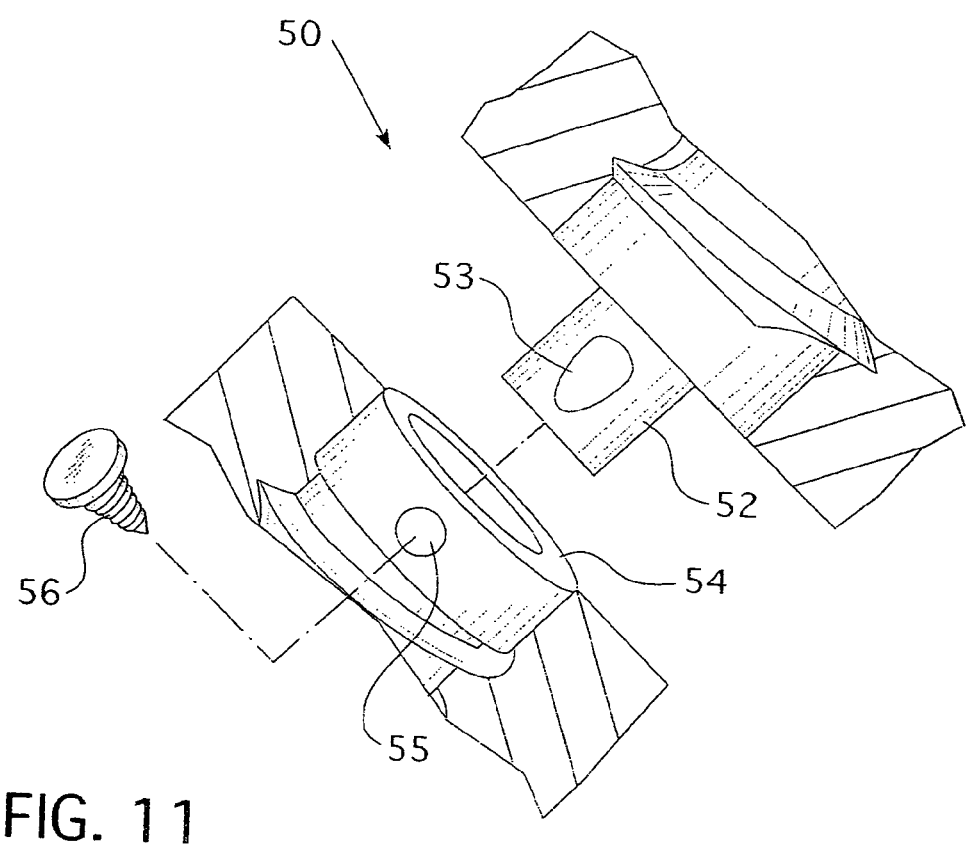
FIG. 11 is a perspective view of a third embodiment of the invention having another variation on an interface coupling arrangement.

FIG. 11 illustrates a third embodiment 50 of the invention having a third variant interface coupling arrangement. In FIG. 11, the upper interface 52 contains an upper interface paraboloidal aperture 53 part-way or completely through the upper interface 52. For example, if the upper interface 52 is annular, the upper interface paraboloidal aperture 53 extends through at least one of the annular walls; if the upper interface 52 is solid, the upper interface paraboloidal aperture 53 extends part-way or completely through the upper interface 52. The lower interface 54 is annular and at least one wall of the lower interface 54 includes a lower interface circular aperture 55. The two apertures receive a tapered screw 56 to secure and to draw the upper interface 52 and the lower interface 54 together. As the tapered screw 56 advances through the lower interface circular aperture 55 and then through the upper interface paraboloidal aperture 53, the upper interface 52 is drawn (pulled) further into engagement with the lower interface 54 as the upper interface 52 moves to allow the upper interface paraboloidal aperture 53 to accommodate the increasing diameter of the tapered screw 56 as it is inserted. The net effect is to produce a compression force at the interface of the two bone segments on both sides of the joint or bone pieces to be joined.

The present invention may be used to fuse virtually any two bones or bone fragments, but the particular advantages of the present implants in small bones is apparent from the above.

In one embodiment of the invention, the direct fastening components (such as the mating pins 26) may be made of a material which responds to a magnetic field, such as iron, iron alloy or other material which responds to magnetic force. If the only the actual fastening components and not the entire implantable components are susceptible to magnetic force, then an external magnetic field may be used to rotate the inventive components into final interlocked alignment, rather than digital manipulation and rotation by the surgeon. Although most joints to be fused with the present invention may be manipulated and rotated into final position digitally, in some instances it is advantageous to rotate the mating pins into position without touching or stressing the adjacent tissues, such as for example and without limitation when there is tissue damage adjacent the bones to be fused or when the bones are so small the computer-assisted rotation with a robotic, non-contacting magnetic field can be more precise than manual manipulation.

The components of the present invention may be fabricated from any material suitable for bone implants, including but not limited to surgical stainless steel and titanium alloys known for use in the manufacture of bone screws. In certain instances it is possible to fabricate the present components from polymers including but not limited to polyurethane, polypropylene or polyethylene terephthalate, or composite materials containing a mixture of powdered bone, powdered metal, polymer or combinations or sintered combinations thereof. The preferred material for use in manufacturing the present components is titanium alloy.

Although the invention has been described particularly above, in connection with specific disclosures and embodiments, alternatives and variations, the invention is only to be limited insofar as set forth in the accompanying claims.

The invention claimed is:

1. A two-component system for joining two hand or foot bones or bone fragments, consisting of: a first component which is threaded, self-tapping and bears an annular mating end having two L-shaped slots on opposite sides thereof; and a second component which is threaded, self-tapping and bears two mating pins at its free end, wherein each component bears both continuous threads and interrupted threads, wherein the threads of the first component have opposite handedness to the threads of the second component, wherein said annular mating end and said two mating pins and a screwdriver slot are made of a material which responds to a magnetic field, and further wherein said annular mating end and said two mating pins each have a diameter or span no greater than the largest diameter of its respective component and are both engageable and reopenable both to bring said two bones or bone fragments into compressive engagement and also to allow reopening of said two-component system for individual removal of said first component and said second component from adjacent bone as needed, and further wherein said two mating pins are positioned in line.

* * * * *